United States Patent [19]

Wohltjen

[11] Patent Number: 4,572,900

[45] Date of Patent: Feb. 25, 1986

[54] ORGANIC SEMICONDUCTOR VAPOR SENSING METHOD

[75] Inventor: Henry Wohltjen, Burke, Va.

[73] Assignee: The United States of America as represented by the Secretary of the Navy, Washington, D.C.

[21] Appl. No.: 603,874

[22] Filed: Apr. 25, 1984

[51] Int. Cl.$^4$ .............................. G01N 27/16
[52] U.S. Cl. ...................... 436/151; 73/23; 324/65 R; 422/94; 422/98; 436/152
[58] Field of Search ............... 73/23; 324/71.5, 65 R; 340/632–634; 422/94, 95, 98; 436/149, 151, 152

[56] References Cited

U.S. PATENT DOCUMENTS

| 4,112,356 | 9/1978 | Toy | 324/71.5 |
| 4,217,544 | 8/1980 | Schmidt | 324/65 CR |
| 4,350,660 | 9/1982 | Robinson et al. | 422/90 |
| 4,361,802 | 11/1982 | Luijpers | 324/65 R |
| 4,381,922 | 5/1983 | Frey et al. | 422/98 |

FOREIGN PATENT DOCUMENTS

| 7916855 | 1/1981 | France . | |
| 55-149834 | 11/1980 | Japan | 422/94 |
| 55-159146 | 12/1980 | Japan | 73/23 |
| 2077437 | 12/1981 | United Kingdom . | |

OTHER PUBLICATIONS

H. Wohltjen et al., "Chemical Microsensors for Chemical Vapor Detection", Proc. Int. Symp. Protection Against Chemical Warfare Agents, Stockholm, Sweden, Jun. 6–9, 1983, pp. 51–59.

Primary Examiner—Barry S. Richman
Assistant Examiner—Michael S. Gzybowski
Attorney, Agent, or Firm—Robert F. Beers; William T. Ellis

[57] ABSTRACT

A method and apparatus to automatically compensate for temperature variation in a vapor detection system. In one embodiment, two identical organic semiconductor film sensors in close thermal contact with each other are used in the feedback circuit of an inverting amplifier supplied by constant voltage. One of the sensors is isolated from vapor exposure to act as a reference for the other sensor which is used for vapor sampling. The output of the inverting amplifier provides an indication of the presence and relative concentration of vapor exposure. Variation in sample sensor resistance due to a change in temperature is accompanied by the same corresponding change in the reference sensor, which stabilizes the ratio of the feedback circuit resistances and therefore the gain of the inverting amplifier to exactly compensate for the temperature induced resistance variations automatically.

36 Claims, 3 Drawing Figures

TEMPERATURE BEHAVIOR OF REFERENCED AND UNREFERENCED IRON PHTHALOCYANINE

ORGANIC SEMICONDUCTOR VAPOR SENSING METHOD

BACKGROUND OF THE INVENTION

This invention relates to vapor detection systems and particularly to methods and apparatus for temperature compensated vapor detection.

The electrical resistance sensitivity of organic semiconductor film to vapors is well known. Recently there has been considerable interest toward using the vapor sensitivity of organic semiconductors in micro-sensor applications where detection of a particular vapor is required (see U.S. Pat. No. 4,350,660 to Robinson et al.).

In a typical system, an organic semiconductor film is deposited onto an interdigitated surface conductivity cell, a potential is applied and the resulting current flow is measured. Variations in the current flow with changes in the vapor exposed to the device signal the presence of specific vapors or classes of vapors.

There are two serious problems encountered with this technique. First, the films have very high resistances even when used with the interdigitated electrodes. This necessitates the use of comparably high value resistors to provide a measurement reference whether used in a simple voltage divider, a wheatstone bridge or current-to-voltage converter circuit. Such high value resistors are physically large, expensive and somewhat unstable with time. The second problem is that the conductivity of the semiconductor film is highly temperature sensitive. Thus, it is very difficult to discriminate between signal changes caused by small temperature variations and those caused by small vapor concentration changes. Yet a third problem is that the aforesaid techniques requiring high value reference resistors are not suitable for the microfabrication which is necessary for mass production of economical and reliable devices.

The prior art has dealt with the problem of temperature compensation a number of different ways.

U.S. Pat. No. 4,112,356 to Toy discloses a semiconductor vapor detector circuit having automatic temperature compensation which relies upon the principle of swamping out the temperature coefficient of one critical element with the temperature coefficient of another component having opposite polarity. In this case, the semiconductor sensor has a negative coefficient. An operational amplifier for amplifying the detector output is selected having a positive temperature coefficient. A portion of the output signal derived by resistance voltage division, along with a resistance generated voltage proportional to amplifier supply current, is negatively fed back to the amplifier input. The negative feedback generated by returning a certain amount of signal proportional to both amplifier output and supply current can be adjusted by resistance voltage division so that the temperature coefficient effects of the amplifier should cancel the temperature coefficient of the semiconductor vapor sensor. However, this system has some serious shortcomings. First, a combination of resistance voltage dividers must be used to properly balance the temperature coefficients of the sensor and amplifier, increasing complexity and making the apparatus more difficult to fabricate, especially if it is to be fabricated on an integrated circuit. In addition, unless the components for the system are manufactured to extremely narrow tolerances, the resistance voltage division circuitry will have to be adjustable. This adds to cost and complexity, and prohibits microfabrication as well. Finally, the operational amplifier must operate under the same ambient conditions as the sensor itself. This limitation can increase cost and fabrication problems for some applications.

U.S. Pat. No. 4,361,802 to Luippers discloses another system of temperature compensation using resistance wires for vapor analysis. A wire element is used in each leg of a bridge circuit, two of the elements in opposite legs of the bridge being exposed to the vapor to be measured, and the remaining two elements being exposed to a reference vapor. The difference in thermal conductivity between the sampled vapor and the reference causes an imbalance in the bridge and a corresponding voltage developed on its output. To ensure that the reference elements retain the same resistance under varying thermal conditions, the current to the bridge is controlled by connecting this primary bridge in one leg of a secondary bridge circuit, using the resistance of the primary bridge to control a current regulator circuit to keep the current fed to the primary bridge constant, thereby providing temperature compensation for any thermally induced resistance shift. This system could be adapted for semiconductor vapor sensors, but it has several disadvantages. First, it requires the use of four sensor elements, two of which must be exposed to a reference gas. It also requires the use of a secondary bridge circuit and associated current control circuitry, which requires the use of thermally stable high impedance resistances, increasing cost and making microfabrication difficult. Finally, unless all components are held to extremely tight tolerances, the secondary bridge must be adjusted and aligned to provide the proper degree of compensation. This reduces economy and reliability of the apparatus and makes microfabrication of the entire circuit impossible U.S. Pat. No. 4,217,544 to Schmidt discloses an automatic temperature compensation system for a corrosion measuring system. This system uses a reference sensor thermally coupled to the active sensor. The reference sensor and associated circuitry generates a signal that is proportional to temperature. This temperature signal is then subtracted from the uncompensated output signal from the active sensor circuitry to produce a temperature compensated output. This system has significant problems if adapted for temperature compensation using semiconductor vapor sensors. First, both the active and reference sensors must have preamplification, requiring a multiplicity of operational amplifiers and associated high impedance resistances. This increases cost and complexity, and if the circuit is to be microfabricated onto a single integrated circuit, the amplifiers and resistances must have a high degree of thermal stability as well, driving up cost still further. In addition, the reference temperature signal and the uncompensated active sensor signal must be balanced in the subtractor circuit for the proper degree of temperature compensation, making entire fabrication of the circuit onto single integrated circuit impossible and requiring the use of external calibration controls, thereby increasing cost and complexity.

OBJECTS OF THE INVENTION

Accordingly, one object of the present invention is to automatically compensate a vapor detection system for the temperature-induced variation in output from organic semiconductor film vapor sensors.

Another object of the present invention is to economize the fabrication of a temperature compensated organic semiconductor film sensor type vapor detection system.

Yet another object if the present invention is to simplify the circuitry of a temperature compensated organic semiconductor film sensor type vapor detection system.

A further object of the present invention is to eliminate calibration adjustments in a temperature compensated organic semiconductor film sensor type vapor detection system.

A still further object of the present invention is to adapt the circuitry of a temperature compensated organic semiconductor film sensor type vapor detection system for fabrication onto a single integrated circuit.

SUMMARY OF THE INVENTION

The present invention achieves automatic temperature compensation and gain control for a vapor sensing system using an organic semiconductor film type vapor sample sensor as one gain controlling resistance for negative feedback in an inverting amplifier. A resistance having an identical temperature coefficient, such as a matching organic semiconductor film sensor having an isolation barrier to prevent vapor contact, is used as the other gain controlling resistance. If the inverting amplifier is fed by a constant electric potential source, the amplifier output will change only due to vapor induced resistance change in the sample sensor, the feedback circuit stabilizing system gain by using temperature induced resistivity changes in the reference resistance to exactly cancel temperature induced resistivity changes in the sample sensor.

Because the inverting amplifier circuit may be a simple operational amplifier, the entire invention may be fabricated onto a single integrated circuit. No calibration controls or resistor networks are required for circuit operation.

The foregoing, as well as other objects, features and advantages of the invention will be apparent from the following description of several embodiments of the invention, and the novel features will be particularly pointed out hereinafter in connection with the appended claims.

DETAILED DESCRIPTION OF THE INVENTION

Figure 1:
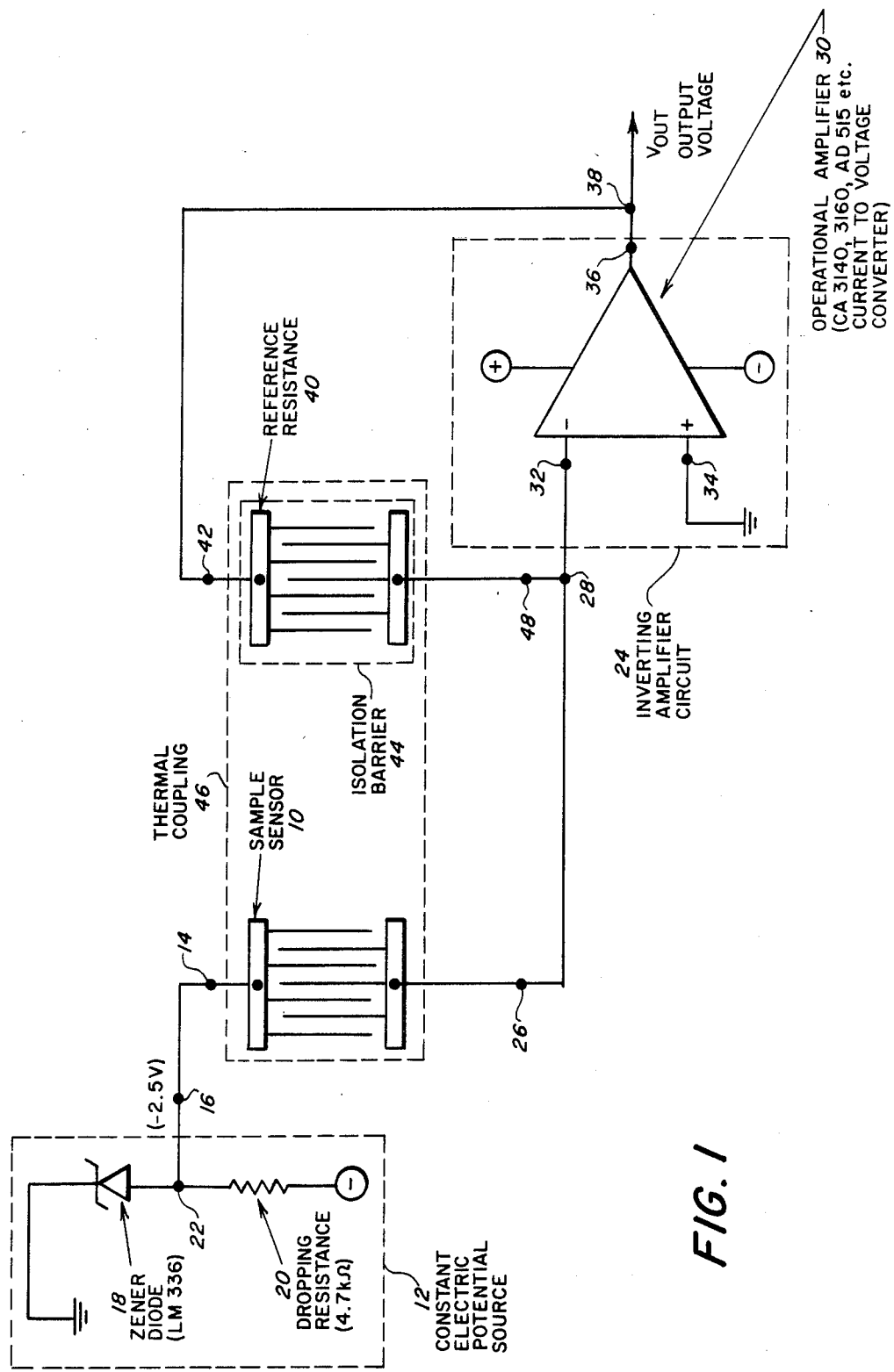
FIG. 1 is a schematic diagram of the circuit used for one embodiment of the present invention.

Referring to the drawings, wherein reference characters designate like or corresponding parts throughout the views, FIG. 1 shows the schematic for one embodiment of the invention. A vapor sample sensor which is to be temperature compensated is illustrated in the figure, by way of example, as an interdigitated surface conductivity cell coated with an iron-phthalocyanine film. Any other organic semiconductor film sensitive to vapor may be substituted, such as any other metal-phthalocyanine film, especially one having a metal constitutent of copper, nickel, lead, manganese or cobalt. Any other types of vapor sensors may be used as well, as long as their resistivities are proportional to the concentration of vapor exposure. Sample sensor 10 is connected to a constant electric potential source 12 via an electrode 14 from sample sensor 10 to an output terminal 16 from constant electric potential source 12. Constant electric potential source 12 is illustrated, by way of example, as a voltage regulator circuit comprising a zener diode 18 and a dropping resistance 20 having an output terminal 22 connected to terminal 16. Any other source of constant potential may be substituted such as a battery. Sample sensor 10 is connected to an inverting amplifier circuit 24 via an electrode 26 from sample sensor 10 to an input terminal 28 from inverting amplifier circuit 24. In a preferred embodiment, inverting amplifier circuit 24 comprises an operational amplifier 30 having a negative input terminal 32 connected to terminal 28, a positive input terminal 34 connected to ground potential and an output terminal 36 connected into an amplifier output terminal 38 of inverting amplifier circuit 24. Inverting amplifier circuit 24 produces an output potential $V_{out}$ which is connected to a reference resistance 40 via terminal 38 from inverting amplifier circuit 24 to an electrode 42 from reference resistance 40. For convenience, reference resistance 40, as illustrated in the figure, may be identical to sample sensor 10, if reference resistance 40 is used in conjunction with an isolation barrier 44 to prevent vapor contact with reference resistance 40. Alternatively, any other reference resistance may be used as long as its temperature coefficient characteristics match sample sensor 10. Isolation barrier 44 is illustrated in FIG. 1 by the dashed-line box surrounding reference resistance 40. It may comprise an inert passivating film, such as teflon or parafin. Any covering that provides a vapor tight seal may be substituted, as well as a separate isolation chamber. Isolation barrier 44 may be deleted if a vapor insensitive material is chosen for reference resistance 40. Reference resistance 40 and sample sensor 10 are thermally connected by a thermal coupling 46, shown in FIG. 1 as a dashed-line box surrounding both sample sensor 10 and reference resistance 40. Thermal coupling 46 is illustrated, by way of example, as a common substrate for sample sensor 10 and reference resistance 40. Any other type of thermal coupling, such as a metal heat sink, may be substituted. Reference resistance 40 is connected to the input of inverting amplifier circuit 24 via an electrode 48 from reference resistance 40 to input terminal 28 from inverting amplifier circuit 24.

$V_{out}$ represents the output signal proportional in electric potential only to the vapor induced change in electrical resistivity of sample sensor 10, corresponding to:

$$V_{out} = (R_{REF}/R_{SAMPLE})(-V_{REF})$$

$V_{out}$ = voltage output of operational amplifier
$V_{REF}$ = voltage output of voltage regulator circuit
$R_{REF}$ = resistance of reference sensor
$R_{SAMPLE}$ = resistance of sample sensor.

The voltage output of the system is proportional to the change in resistance in sample sensor 40, and any thermal variations in resistance of sample sensor 10 are cancelled by a corresponding change in resistance of reference resistance 40. A voltage output signal is thereby produced which is proportional to the change in sample sensor resistance and free from shift in system gain, and therefore output, caused by temperature variation. The only requirements of the system outside of those aforesaid are that the voltage regulator circuit output be moderately stable, in the range of 0.01%/C.° or less, and that the operational amplifier have an input bias current compatible with the resistance of the sensor to minimize resulting offset voltage in the output, a few picoamperes or less.

Figure 3:
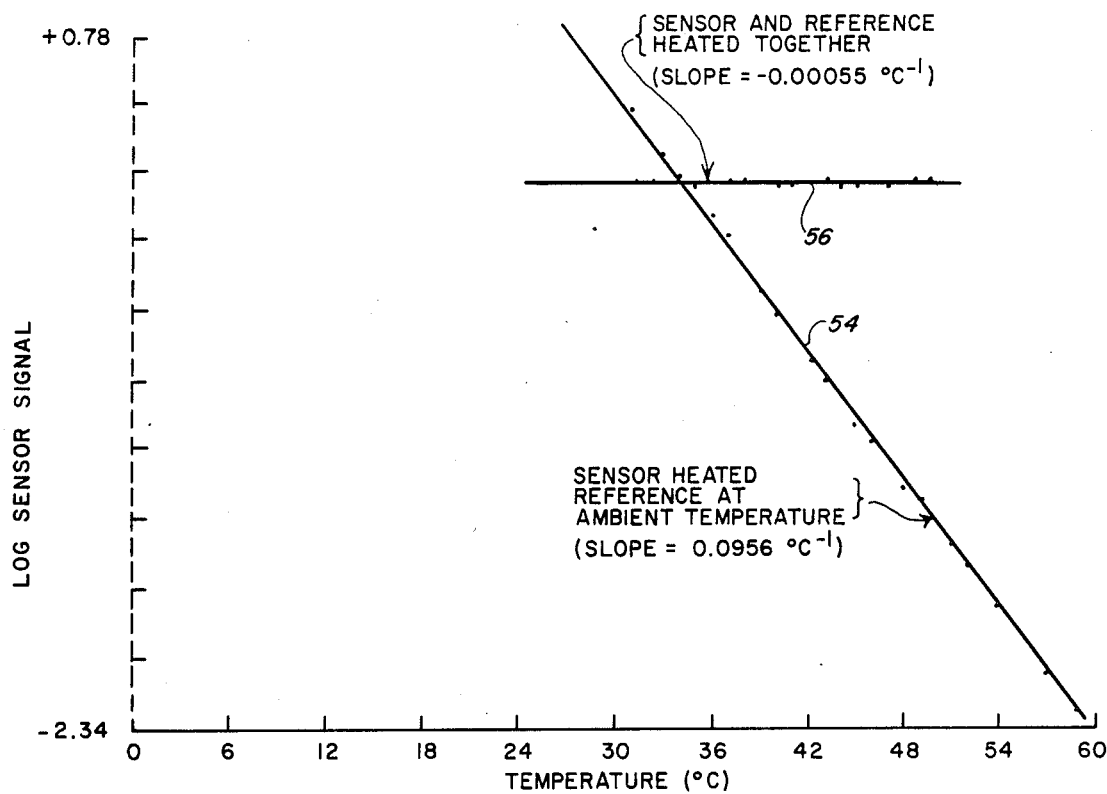
FIG. 3 is a graphical representation of an organic semiconductor film vapor sensor response with and without the temperature compensation provided by the present invention.

The operation of the invention is illustrated in FIG. 3. In FIG. 3, the inverted slope plot 54 of sensor voltage versus temperature represents the output of the organic semiconductor film vapor sensor system without temperature compensation.

The horizontal line plot 56 of sensor response versus temperature represents the temperature compensated system output, and shows how the invention eliminates sensitivity of the vapor detection system to temperature variation. Output of the temperature compensated system is virtually constant regardless of temperature.

Figure 2:
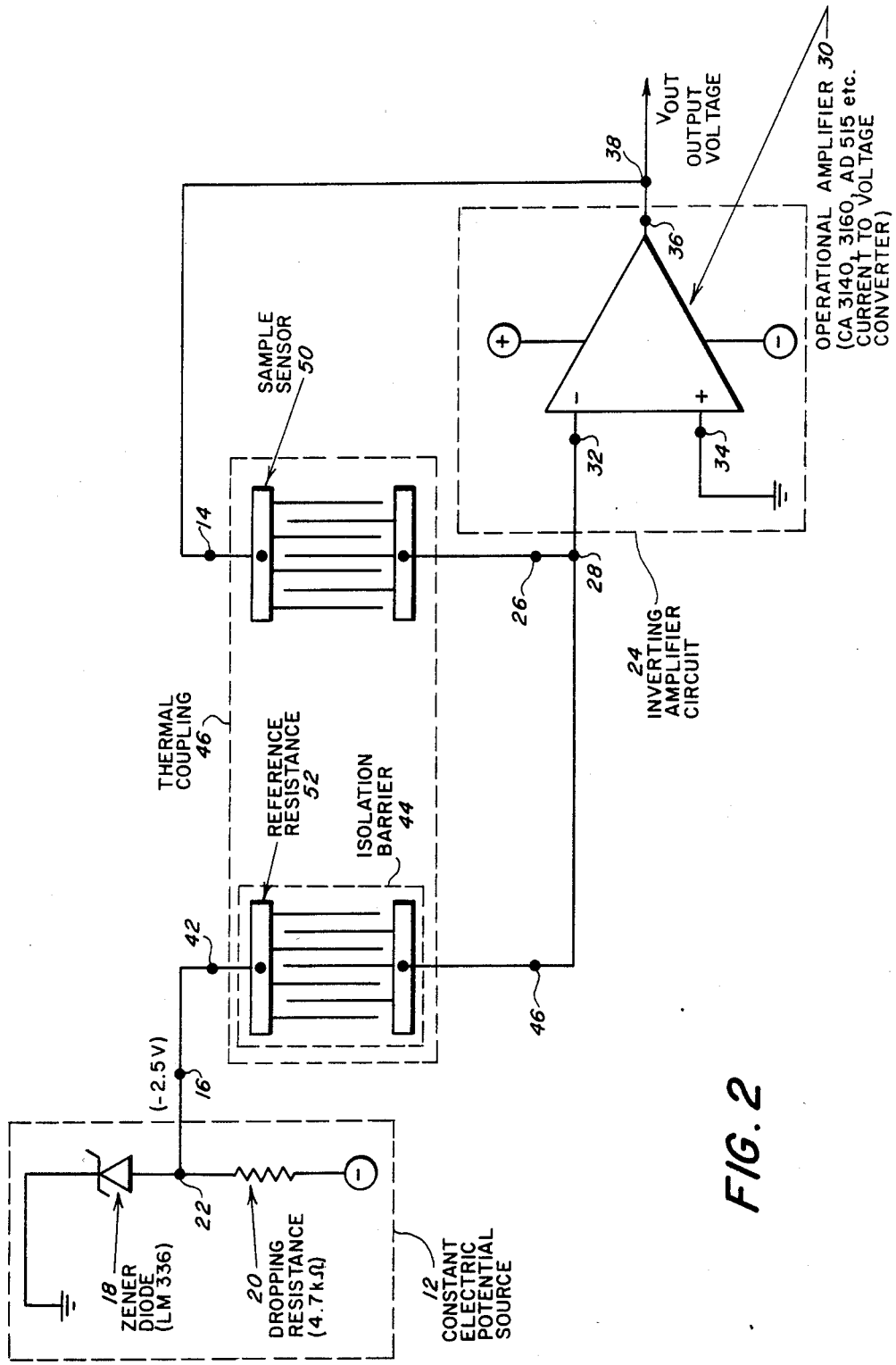
FIG. 2 is a schematic diagram of the circuit for another embodiment of the present invention.

A second embodiment of the invention is illustrated by the schematic diagram of FIG. 2. The second embodiment comprises a rearrangement of the components utilized in the first embodiment described above, wherein sample sensor 10 of FIG. 1 takes the position of reference resistance 40 and is redesignated as a sample sensor 50, and reference resistance 40 of FIG. 2 takes the position of sample sensor 10 and is redesignated as a reference resistance 52.

Sample sensor 50 is connected to the input of inverting amplifier circuit 24 via electrode 26 from sample sensor 50 to input terminal 28 from inverting amplifier circuit 24. In a preferred embodiment, inverting amplifier circuit 24 comprises operational amplifier 30 having a negative input terminal 32 connected to terminal 28, a positive input terminal 34 connected to ground potential and output terminal 36 connected to amplifier output terminal 38 of inverting amplifier circuit 24. Inverting amplifier circuit 24 produces an output potential $V_{out}$ which is connected to sample sensor 50 via terminal 38 from inverting amplifier circuit 24 to electrode 14 from sample sensor 50. Reference resistance 52 is connected to constant electric potential source 12 via electrode 42 from reference resistance 52 to output terminal 16 from constant voltage source 12. Constant electric potential source 12 is illustrated, by way of example, as comprising zener diode 19 and dropping resistance 20 having output terminal 22 connected to terminal 16. Reference resistance 52 is connected to the input of inverting amplifier circuit 24 via electrode 46 from reference resistance 52 to input terminal 28 from inverting amplifier circuit 24. Reference resistance 52 is thermally coupled to sample sensor 50 by thermal coupling 46 and isolated from vapor contact by isolation barrier 24.

$V_{out}$ represents the output signal proportional in electric potential only to the vapor induced change in electrical resistivity of sample sensor 50, corresponding to:

$$V_{out} = (R_{SAMPLE}/R_{REF})(-V_{REF})$$

$V_{out}$ = voltage output of operational amplifier
$V_{REF}$ = voltage output of voltage regulator circuit
$R_{REF}$ = resistance of reference sensor
$R_{SAMPLE}$ = resistance of sample sensor As with the first embodiment described above, the voltage output of the system is proportional to the change in resistance in the sample sensor 50, however, the voltage versus vapour concentration slope is inverted.

It will be understood that various changes in the details, materials and arrangements of parts which have been herein described and illustrated in order to explain the nature of the invention may be made by those skilled in the art within the principle and scope of the invention as expressed in the appended claims.

What is claimed and desired to be secured by Letters Patent of the United States is:

1. A vapor detection apparatus having automatic temperature compensation comprising:
vapor sensitive variable electric resistance means for detecting the presence of vapor;
reference electrical resistance means having a temperature coefficient corresponding to said vapor sensitive resistance means for balancing thermal variation of said vapor sensitive resistance means;
coupling means thermally coupling said vapor sensitive resistance means and said reference resistance means;
electric potential means for generating a first current signal through one of said resistance means; and
electrical current-to-potential converting means for generating a second current signal through the other of said reistance means and developing an electric output potential inversely proportional to said first current signal combined with said second current signal.

2. The vapor detection apparatus according to claim 1, wherein said vapor sensitive variable electrical resistance means comprises an organic semiconductor film sensor.

3. The vapor detection apparatus according to claim 2, wherein said reference electrical resistance means comprises a vapor sensitive organic film sensor with isolation means for blocking vapor contact.

4. The vapor detection apparatus according to claim 3, wherein said organic film sensors each comprise an organic semiconductor film deposited onto an interdigitated surface conductivity cell.

5. The vapor detection apparatus according to claim 4, wherein said electric potential means comprises a constant voltage source.

6. The vapor detection apparatus according to claim 5, wherein said electric potential means comprises a constant voltage regulator.

7. The vapor detection apparatus according to claim 6, wherein said electrical current-to-potentital means comprises an operational amplifier.

8. The vapor detection apparatus according to claim 7, wherein said coupling means comprises a heat sink.

9. The vapor detection apparatus according to claim 8, wherein said heat sink comprises a common substrate for said organic semiconductor film sensors.

10. The vapor detection apparatus according to claim 9, wherein said isolation means comprises an inert passivating film covering.

11. The vapor detection apparatus according to claim 10, further comprising electric potential sensing means for determining the level of said potential output.

12. The vapor detection apparatus according to claim 11, wherein said electric potential sensing means comprises a voltmeter.

13. The vapor sensing apparatus according to claim 12, wherein said organic semiconductor films each comprise a metal-phthalocyanine film wherein one constituent of said metal-phthalocyanine film is a metal.

14. The vapor sensing apparatus according to claim 13, wherein said metal is selected from the group consisting of copper, nickel, iron, lead, manganese and cobalt.

15. The vapor sensing apparatus according to claim 13, wherein said metal comprises iron.

16. A temperature compensated vapor detection circuit for a vapor analysis system comprising:
a voltage regulator circuit having a regulated output:
an operational amplifier having a negative input, a positive input connected to ground potential and an amplifier output having an electric potential output inversely proportional to current fed into said negative input;
a vapor sensor having electrical resistance proportional to vapor exposure connected between said regulated output and said negative input;
an electrical reference resistance having a temperature coefficient corresponding to said vapor sensor connected between said amplifier output and said negative input;
a thermal coupling thermally linking said reference resistance to said vapor sensor:
a vapor isolation barrier for protecting said reference resistance from exposure to vapor; and
an electric potential output sensor connected to said amplifier output.

17. The vapor detection circuit according to claim 16, wherein said vapor sensor comprises an organic semiconductor film deposited onto an interdigitated surface conductivity cell.

18. The vapor detection circuit according to claim 17, where said reference resistance comprises an organic semiconductor film deposited onto an interdigitated surface conductivity cell.

19. The vapor detection circuit according to claim 18, wherein said vapor isolation barrier comprises an inert passivating film coating over said reference resistance.

20. The vapor detection apparatus according to claim 19, wherein said thermal coupling comprises a common substrate for said vapor sensor and said reference resistance.

21. The vapor detection apparatus according to claim 20, wherein said electrical potential output sensor comprises a voltmeter.

22. The vapor detection circuit according to claim 21, wherein said organic semiconductor films each comprise a metal-phthalocyanine film wherein one constituent of said metal-phthalocyanine film is a metal.

23. The vapor detection circuit according to claim 22, wherein said metal is selected from the group consisting of copper, nickel, iron, lead, manganese and cobalt.

24. The vapor detection circuit according to claim 22, wherein said metal comprises iron.

25. A temperature compensated vapor detection circuit for a vapor analysis system comprising:
a voltage regulator circuit having a regulated output;
an operational amplifier having a negative input, a positive input connected to ground potential and an amplifier output having an electric potential output inversely proportional to current fed into said negative input;
a vapor sensor having electrical resistance proportional to vapor exposure connected between said amplifier output and said negative input;
an electrical reference resistance having a temperature coefficient corresponding to said vapor sensor connected between said regulated output and said negative input;
a thermal coupling thermally linking said reference resistance to said vapor sensor;
a vapor isolation barrier for protecting said reference resistance from exposure to vapor; and
an electric potential output sensor connected to said amplifier output.

26. The vapor detection circuit according to claim 25, wherein said vapor sensor comprises an organic semiconductor film deposited onto an interdigitated surface conductivity cell.

27. The vapor detection circuit according to claim 26, wherein said reference resistance comprises an organic semiconductor film deposited onto an interdigitated surface conductivity cell.

28. The vapor detection circuit according to claim 27, wherein said vapor isolation barrier comprises an inert passivating film coating over said reference resistance.

29. The vapor detection apparatus according to claim 28, wherein said thermal coupling comprises a common substrate for said vapor sensor and said reference resistance.

30. The vapor detection apparatus according to claim 29, wherein electrical potential output sensor comprises a voltmeter.

31. The vapor detection circuit according to claim 30, wherein said organic semiconductor films each comprise a metal-phthalocyanine film wherein one constituent of said metal-phthalocyanine film is a metal.

32. The vapor detection circuit according to claim 31, wherein said metal is selected from the group consisting of copper, nickel, iron, lead, manganese and cobalt.

33. The vapor detection circuit according to the claim 31, wherein said metal comprises iron.

34. A method of vapor detection having automatic temperature compensation comprising:
selecting a vapor sensitive variable electrical resistance means for detecting the presence of vapor;
selecting a reference electrical resistance means having a temperature coefficient corresponding to said vapor sensitive resistance means, isolation from vapor contact and thermally coupled to said vapor sensitive resistance means;
generating a first current signal through one of said resistance means with the application of a constant electric potential:
generating a second current signal through the other of said resistance means with the application of an electric output potential proportional to said first current signal combined with said second signal;
converting said first current signal combined with said second current signal into said electric output potential; and
measuring said electric potential output.

35. A method of vapor detection according to claim 34 wherein the step of selecting said vapor sensitive resistance means comprises the step of selecting said vapor sensitive resistance means from the class of vapor sensitive organic semiconductor film resistances.

36. A method of vapor detection according to claim 35, wherein the step of selecting said reference resistance means comprises the steps of:
selecting said reference means from the class of vapor sensitive organic film resistance;
isolating said reference resistance means from vapor contact; and
coupling said reference resistance means to said vapor sensitive resistance means thermally.

* * * * *